United States Patent
Gleich et al.

(10) Patent No.: US 8,368,394 B2
(45) Date of Patent: *Feb. 5, 2013

(54) ARRANGEMENT AND METHOD FOR INFLUENCING AND/OR DETECTING MAGNETIC PARTICLES IN A REGION OF ACTION

(75) Inventors: Bernhard Gleich, Hamburg (DE); Juergen Weizenecker, Hamburg (DE); Juergen Kanzenbach, Itzstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 442 days.

This patent is subject to a terminal disclaimer.

(21) Appl. No.: 12/519,769

(22) PCT Filed: Dec. 14, 2007

(86) PCT No.: PCT/IB2007/055126
§ 371 (c)(1),
(2), (4) Date: Oct. 13, 2009

(87) PCT Pub. No.: WO2008/078242
PCT Pub. Date: Jul. 3, 2008

(65) Prior Publication Data
US 2010/0052668 A1 Mar. 4, 2010

(30) Foreign Application Priority Data
Dec. 20, 2006 (EP) ..................... 06126569

(51) Int. Cl.
*G01N 27/72* (2006.01)
*G01R 33/12* (2006.01)
(52) U.S. Cl. ...................................... 324/228
(58) Field of Classification Search .................... None
See application file for complete search history.

(56) References Cited

U.S. PATENT DOCUMENTS
(Continued)

FOREIGN PATENT DOCUMENTS
DE 10151778 5/2003
EP 1145738 10/2001
(Continued)

OTHER PUBLICATIONS
Gleich, B., et al., "Magnetic Particle Imaging (MPI)", MEDICAMUNDI, vol. 50, No. 1, May 1, 2006, pp. 66-71.
(Continued)

*Primary Examiner* — Roberto Velez

(57) ABSTRACT

An arrangement and a method for influencing and/or detecting magnetic particles in a region of action is disclosed, which arrangement comprises: —selection means for generating a magnetic selection field having a pattern in space of its magnetic field strength such that a first sub-zone having a low magnetic field strength and a second sub-zone having a higher magnetic field strength are formed in the region of action, —drive means for changing the position in space of the two sub-zones in the region of action by means of a magnetic drive field so that the magnetization of the magnetic particles changes locally, —receiving means for acquiring signals, which signals depend on the magnetization in the region of action, which magnetization is influenced by the change in the position in space of the first and second sub-zone, wherein the selection means and/or the drive means and/or the receiving means comprises at least partially a litz wire/stranded wire.

15 Claims, 5 Drawing Sheets

U.S. PATENT DOCUMENTS

| | | | | |
|---|---|---|---|---|
| 3,487,385 | A | * | 12/1969 | Sakai ............................... 365/61 |
| 3,783,179 | A | * | 1/1974 | Ferber et al. ............... 174/121 A |
| 4,549,042 | A | * | 10/1985 | Akiba et al. ............... 174/114 R |
| 4,963,694 | A | | 10/1990 | Alexion et al. |
| 5,517,755 | A | * | 5/1996 | Wright ............................. 29/843 |
| 6,724,191 | B1 | * | 4/2004 | Larsen .......................... 324/329 |
| 6,787,948 | B2 | * | 9/2004 | Peterson et al. ................ 310/58 |
| 6,845,262 | B2 | * | 1/2005 | Albert et al. .................. 600/420 |
| 7,370,656 | B2 | * | 5/2008 | Gleich et al. .................. 128/899 |
| 7,778,681 | B2 | * | 8/2010 | Gleich .......................... 600/407 |
| 8,044,660 | B2 | * | 10/2011 | Gleich et al. .................. 324/228 |
| 2001/0012915 | A1 | * | 8/2001 | Avrin et al. .................... 600/424 |

FOREIGN PATENT DOCUMENTS

| | | |
|---|---|---|
| EP | 1304542 | 4/2003 |
| JP | 11232936 A | 8/1999 |
| WO | WO 2004091392 A1 * | 10/2004 |
| WO | 2006067692 | 6/2006 |

OTHER PUBLICATIONS

Sullivan, C.R., "Optimal Choice for Number of Strands in a Litz-Wire Transformer Winding", IEEE Transactions on Power Electronics, IEEE Service Center, Piscataway, NJ, US, vol. 14, No. 2, Mar. 1, 1999, XP011043290.

* cited by examiner

ARRANGEMENT AND METHOD FOR INFLUENCING AND/OR DETECTING MAGNETIC PARTICLES IN A REGION OF ACTION

CROSS REFERENCE TO RELATED APPLICATIONS

This application claims the benefit of EP provisional application s/n 06126569.0, filed Dec. 20, 2006, which is incorporated herein by reference. Related applications are: PCT s/n IB2007/055152, "Arrangement for Influencing and/or Detecting Magnetic Particles in a Region of Action and Method of Producing a Disk Shaped Coil," filed Dec. 17, 2007, PCT s/n IB2007/055157, "Arrangement and Method for Influencing and/or Detecting Magnetic Particles in a Region of Action," filed Dec. 17, 2007, PCT s/n IB2007/055134, "Arrangement and Method for Influencing and/or Detecting Magnetic Particles in a Region of Action," filed Dec. 14, 2007, PCT s/n IB2007/055174, "Arrangement and Method for Influencing and/or Detecting Magnetic Particles in a Region of Action," filed Dec. 17, 2007, PCT s/n IB2007/055131, "Arrangement and Method for Influencing and/or Detecting Magnetic Particles in a Region of Action," filed Dec. 14, 2007, , PCT s/n IB2007/055158, "Arrangement and Method for Influencing and/or Detecting and/or Locating Magnetic Particles in a Region of Action," filed Dec. 17, 2007, PCT s/n IB2007/055162, "Method and Arrangement for Locating Magnetic Markers in a Region of Action," filed Dec. 17, 2007, , PCT s/n IE2007/055178, "Arrangement and Method for Detecting and/or Locating a Magnetic Material in a Region of Action, Use of a Arrangement In the Examination of Buildings," filed Dec. 17, 2007, PCT s/n IE2007/055177, "Method and Arrangement for Influencing and/or Detecting Magnetic Particles in a Region of Action," filed Dec. 17, 2007, PCT s/n IE2007/055204, "Method and Arrangement for Separating Magnetic Particles, Magnetic Particles and Use of Magnetic Particles," filed Dec. 18, 2007, PCT s/n IE2007/055165, "Arrangement and Method for Influencing and/or Detecting Magnetic Particles in a Region of Action, Coil Arrangement," filed Dec. 17, 2007, and PCT s/n IB2007/055163, "Influencing and/or Detecting Magnetic Particles in a Region of Action of a Examination Object," filed Dec. 17, 2007.

The present invention relates to an arrangement for influencing and/or detecting magnetic particles in a region of action. Furthermore, the invention relates to a method for influencing and/or detecting magnetic particles in a region of action.

The arrangement and the method of this kind is known from German patent application DE 101 51 778, A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement and such a method have the advantage that it can be used to examine arbitrary examination objects—e. g. human bodies—in a non-destructive manner and without causing any damage and with a high spatial resolution, both close to the surface and remote from the surface of the examination object.

Known arrangements of this type have shown the disadvantage that coils used to generate a magnetic field or a magnetic field component and/or coils used to detect varying magnetic fields are unsatisfactory, especially in that such coils show a relatively small signal-to-noise ratio.

It is therefore an object of the present invention to provide an arrangement and a method of the kind mentioned initially, in which the quality of the magnetic field generating means and/or the quality of the magnetic field detecting means is improved.

The above object is achieved by an arrangement for influencing and/or detecting magnetic particles in a region of action, wherein the arrangement comprises selection means for generating a magnetic selection field having a pattern in space of its magnetic field strength such that a first sub-zone having a low magnetic field strength and a second sub-zone having a higher magnetic field strength are formed in the region of action, wherein the arrangement further comprises drive means for changing the position in space of the two sub-zones in the region of action so that the magnetization of the magnetic particles changes locally, wherein the arrangement further comprises receiving means for acquiring signals, which signals depend on the magnetization in the region of action, which magnetization is influenced by the change in the position in space of the first and second sub-zone, and wherein the selection means and/or the drive means and/or the receiving means comprises at least partially a litz wire/ stranded wire.

According to the present invention, it is to be understood that the selection means and/or the drive means and/or the receiving means can at least partially be provided in the form of one single coil or solenoid. However, it is preferred according to the present invention that separate coils are provided to form the selection means, the drive means and the receiving means. Furthermore according to the present invention, the selection means and/or the drive means and/or the receiving means can each be composed of separate individual parts, especially separate individual coils or solenoids, provided and/or arranged such that the separate parts form together the selection means and/or the drive means and/or the receiving means. Especially for the drive means and/or the selection means, a plurality of parts, especially pairs for coils (e.g. in a Helmholtz or Anti-Helmholtz configuration) are preferred in order to provide the possibility to generate and/or to detect components of magnetic fields directed in different spatial directions.

According to the present invention, it is preferred that the litz wire comprises a plurality of individual wires, each individual wire being surrounded by an electrically high resistive material. It is thereby possible to provide a very high current supporting surface inside the litz wire which is important both for the case that an AC current with a comparably high frequency is to be supported by the litz wire and for the case that a DC current or an AC current having a comparably low frequency is to be supported by the litz wire but in the presence of a static and/or an dynamic magnetic field that penetrates the litz wire. According to the present invention, it is preferred that the litz wire is spun such that one individual wire is e.g. in the center of the litz wire at one position along the extension direction of the litz wire and that this individual wire is e.g. in the periphery of the litz wire at another position along the extension direction of the litz wire. Thereby it is possible that each one of all the individual wires is preferably provided such that, e.g. in a loop formed by the litz wire, the same impedance is realized by each individual wire.

It is furthermore preferred according to the present invention that the litz wire comprises a plurality of first order litz wires comprising a plurality of individual wires, wherein the litz wire comprises a plurality of first order litz wires. In a preferred embodiment of the present invention, the litz wire comprises a plurality of first order litz wires and a plurality of second order litz wires, wherein the first order litz wires comprise a plurality of individual wires, wherein the second order litz wires comprise a plurality of first order litz wires, and wherein the litz wire comprises a plurality of second order litz wires. Thereby, an increase in current supporting surface is possible and the complexity of the handling requirements—especially the possibility of bending the litz wire (in order to form solenoids or coils) comprising a multitude of individual wires—are reduced.

According to the present invention, it is preferred that the resistance (real part of the impedance) of the receiving means is dominated by thermal noise, especially generated by thermal noise due to the presence of the magnetic particles in the region of action, i.e. the resistance of the current supporting paths without the presence an object (of examination) in the region of action is comparable or smaller than the resistance in presence of an object in the region of action. This is achieved in particular by means of carefully defining the individual current paths (individual wires), current strength, wire configuration and other characteristics of the litz wire of the receiving means.

In still a further preferred embodiment of the present invention, the litz wire comprises at least partially a ferromagnetic material. This is very advantageous in a situation where the ferromagnetic material and the corresponding litz wire serves to guide the magnetic field, especially of the magnetic selection field and/or the magnetic drive field. Preferably, the litz wire containing the ferromagnetic material is positioned at a location where the ferromagnetic material is in saturation.

Furthermore, it is preferred that the litz wire is at least partially used for the selection means and/or for the drive means and that the litz wire of the selections means is at least partially penetrated by the magnetic drive field of the drive means and/or that the litz wire of the drive means is at least partially penetrated by the magnetic selection field of the selection means. The penetration of one of the selection means or the drive means by the magnetic fields of the other component of the inventive arrangement is preferably realized by means of placing the selection means or the drive means penetrated by the magnetic field of the other component in a greater proximity to the region of action than the other component. Thereby, the penetrating magnetic field is comparably strong at the location of the penetrated selection means or drive means. The penetration of the penetrating magnetic field influences the conducting properties of the penetrated selection means or drive means. According to the present invention, it is very advantageous to take into consideration this change in conducting properties of the penetrated selection means or drive means such that the resistance of the selection means or the drive means is as low as possible in the given environment or penetration pattern. The selection means and the drive means together are also called "field generator means". The selection means comprise magnetic field generation means that provide either a static (gradient) magnetic selection field and/or a comparably slowly changing long range magnetic selection field with frequencies in the range of about 1, Hz to about 100, Hz. Both the static part and the comparably slowly changing part of the magnetic selection field can be generated by means of a permanent magnet or by means of coils or by a combination thereof. The drive means comprise magnetic field generation means that provide a magnetic drive field with frequencies in the range of about 1, kHz to about 200, kHz, preferably about 10, kHz to about 100, kHz. At least part of the field generator means (i.e. the selection means and the drive means) can be implemented by discrete coils where the diameter of the individual wires of each coil or of each field generator means has to be chosen in such a way that the skin effect does not increase the resistance of the coil. Normally, the maximum possible wire diameter would be chosen as in that case the filling factor is maximal and therefore the dissipation minimal. However, it is very advantageous in an arrangement according to the present invention that due to the use of litz wire in at least a part of the generator means, the generated magnetic field of one of the generator means (selection means and/or drive means) penetrates the other field generator means (selection means and/or drive means) reducing thereby overall dissipation. In a further preferred embodiment of the present invention, the number of turns of the components of the field generator means, especially the coils, is limited as well as the winding to winding capacitances are minimized. This can be realized by means of a low dielectric constant of the materials between the windings, by the winding in blocks and by a sufficient separation of the windings, especially for the coils of the selection means. One of the advantages of these measures is that within the inventive arrangement, the self-resonances of the individual coils of the field generator means are such that they do not overlap with the drive frequency (except for the coils of the drive means). Such an overlap would cause undesirable field distortions and additional dissipation.

In still a further preferred embodiment of the present invention, the litz wire is arranged such that the resistance in a given working frequency band and in a given electromagnetic field penetrating the litz wire is substantially minimal, i.e. dominated by thermal noise, especially generated by thermal noise due to the presence of the magnetic particles in the region of action, i.e. the resistance of the current supporting paths without the presence an object (of examination) in the region of action is comparable or smaller than the resistance in presence of an object in the region of action. This is achieved in particular by means of carefully defining the individual current paths (individual wires), current strength, wire configuration and other characteristics of the litz wire of the selection means and/or of the drive means.

Furthermore, it is preferred that the litz wire has a ratio of the summed cross sectional area of the individual wires relative to the cross sectional area of the litz wire (filling factor) of about 0.30, to about 0.70,, preferably of about 0.40, to about 0.60, very preferably about 0.50, or wherein the litz wire (250) has a ratio of the summed cross sectional area of the individual wires (255) relative to the cross sectional area of the litz wire (250) (filling factor) of about 0.01, to about 0.20,, preferably of about 0.03, to about 0.10, and/or that the individual wires of the litz wire have a diameter of approximately 1 μm to approximately 50 μm, preferably of approximately 10 μm to approximately 25 μm. It is thereby possible to greatly enhance the used current supporting surface inside the litz wire and therefore to realise a reduced resistance of the overall configuration of the selection means and/or of the drive means and/or of the receiving means. Typically, the filling factor of the litz wire of the selection means and/or of the drive means is in the range of about 0.30, to about 0.70,, preferably in the range of around 0.50,, and therefore higher than the filling factor of the litz wire of the receiving means which is in the range of about 0.01, to about 0.20,, preferably in the range of about 0.03, to about 0.10. Furthermore, the diameter of the individual wires of the litz wire of the selection means and of the drive means can be chosen higher than the diameter of the individual wires of the litz wire of the receiving means.

In a further preferred embodiment of the present invention, the litz wire is a compressed litz wire and/or the litz wire comprises a multitude of thermoplastic resin wires. It is very advantageous that thereby a very dense and stable configuration of the current supporting paths (individual wires) inside the litz wire is possible, thereby decreasing the resistance of the litz wire. Additionally, it is very advantageous that thereby the filling factor of the litz wire can be adjusted to a desired level by varying the pressure of the compression undergone by the litz wire. Furthermore, the filling factor of the litz wire can be adjusted to a desired level by varying the number and/or the size of additional resin wires. These resin wires (thermoplastic wires) are preferably spun together with the individual wires of the litz wire and/or together with the first order litz wires and/or together with the second order litz wires.

According to a further preferred embodiment of the present invention, the space between different litz wires or space inside the litz wire is used for one or a plurality of cooling channels. Thereby, it is advantageously possible to easily define the temperature of the different components of the arrangement according to the present.

Furthermore, it is preferred that the selection means and/or the drive means and/or the receiving means comprises an at least partially disk shaped coil. It is thereby possible to provide coils with an improved performance regarding e.g. the filling factor, the mechanical stability and the possibility for providing a cooling to the current supporting wires.

The present invention further refers to the use of an arrangement according to the present invention and further to a method for influencing and/or detecting magnetic particles in a region of action, wherein the method comprises the steps of
  generating a magnetic selection field having a pattern in space of its magnetic field strength such that a first sub-zone having a low magnetic field strength and a second sub-zone having a higher magnetic field strength are formed in the region of action,
  changing the position in space of the two sub-zones in the region of action by means of a magnetic drive field so that the magnetization of the magnetic particles changes locally,
  acquiring signals, which signals depend on the magnetization in the region of action, which magnetization is influenced by the change in the position in space of the first and second sub-zone,
wherein the generation of the magnetic selection field and/or the change of the position in space of the two sub-zones and/or the selection means and/or the drive means and/or the acquisition of the signals depending on the magnetization in the region of action is performed at least partially by means of a litz wire/stranded wire.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

Figure 4A:
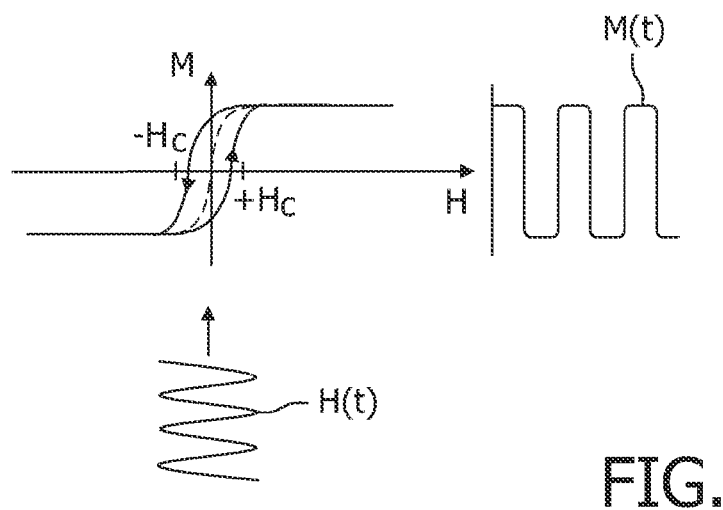
Figure 4B:
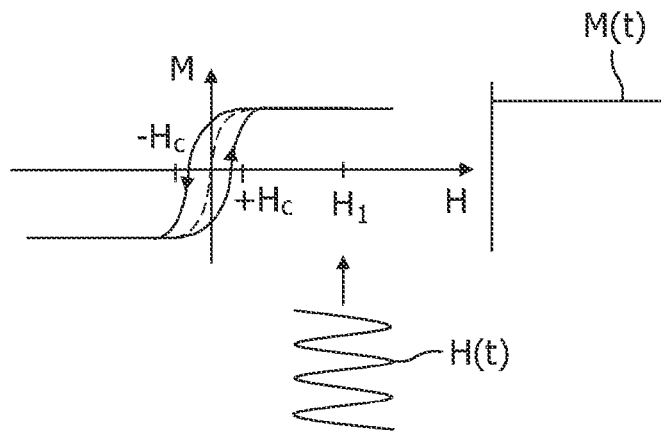

FIGS. 4a, and 4b, illustrate the magnetization characteristics of such particles.

Figure 5:
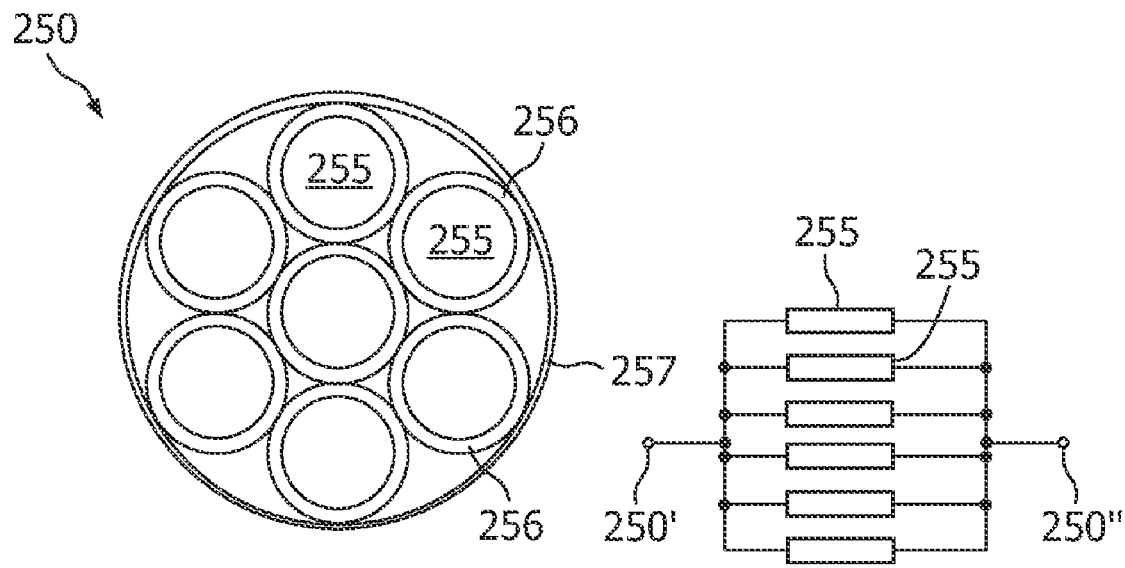
Figure 6:
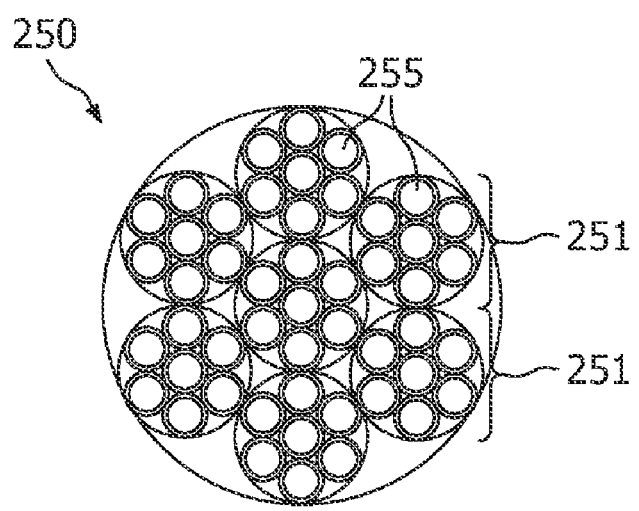
Figure 7:
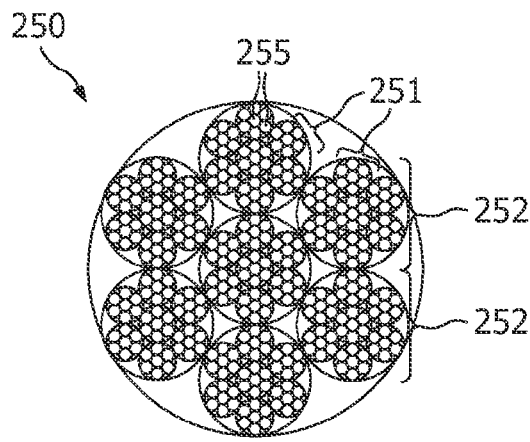

FIGS. 5 to 7 illustrate schematically different examples of litz wire configurations.

FIGS. 8 to 11 illustrate schematically different examples of disk shaped coil configurations.

Figure 12:
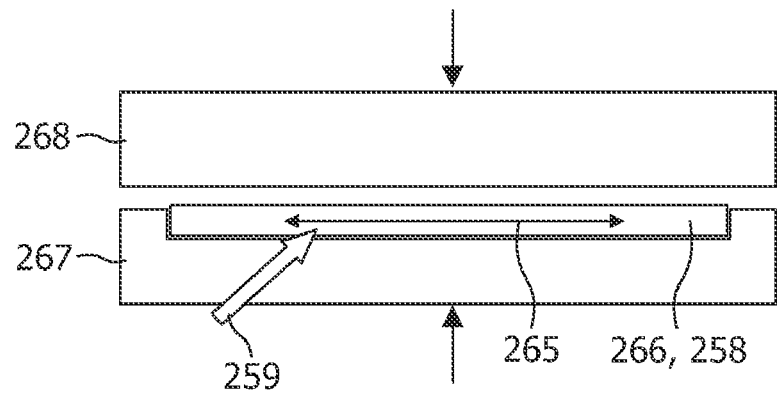

FIG. 12 illustrates schematically an example of a method of producing a disk shaped coil.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1:
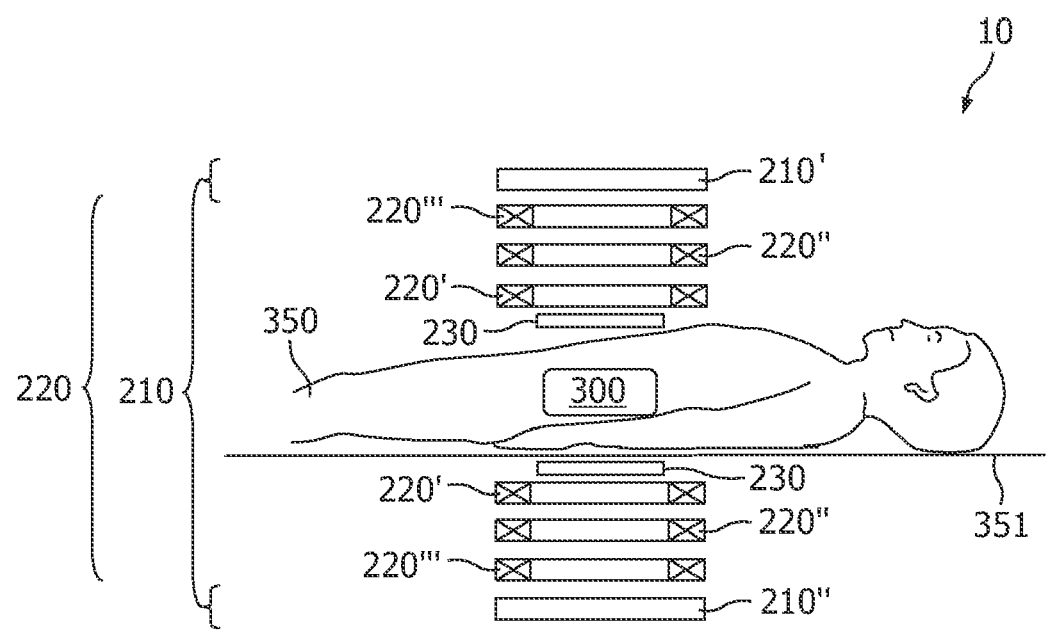
FIG. 1 illustrates an arrangement according to the present invention for carrying out the method according to the present invention.

In FIG. 1, an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
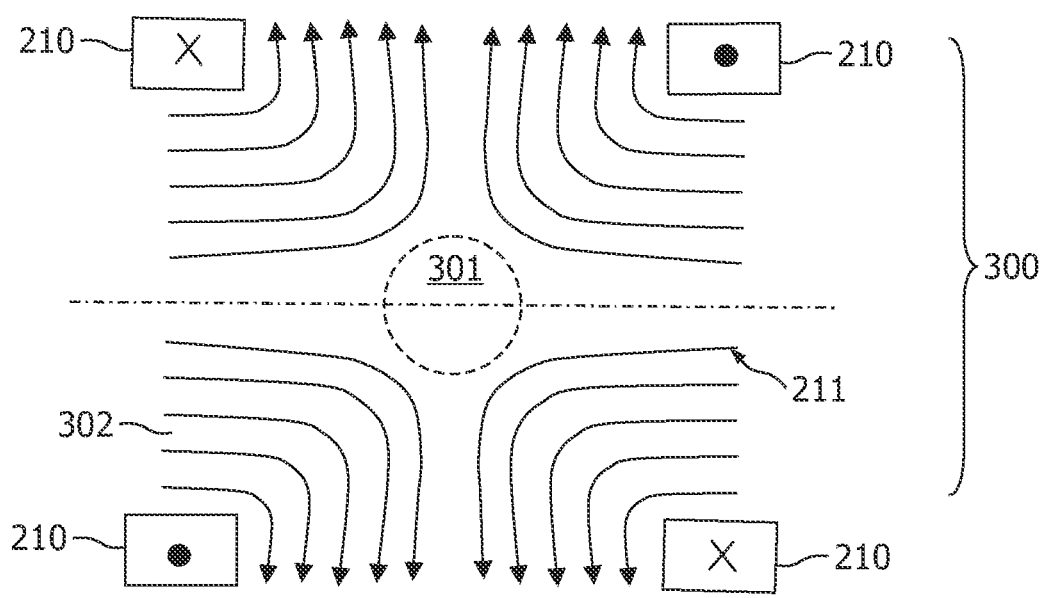
FIG. 2 illustrates an example of the field line pattern produced by an arrangement according to the present invention

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
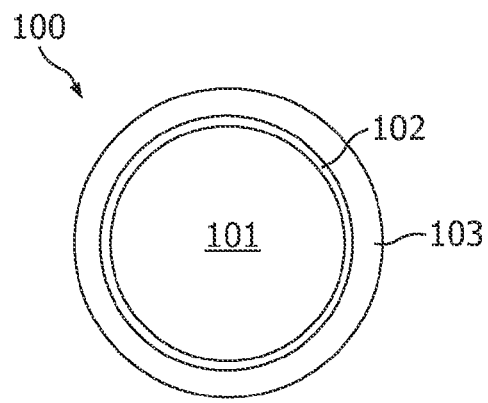
FIG. 3 illustrates an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5, nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 μm, a magnetic field of approximately 800, A/m (corresponding approximately to a flux density of 1, mT) is then required, whereas in the case of a diameter of 100 μm a magnetic field of 80, A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778, are hereby incorporated by reference, especially paragraphs 16, to 20, and paragraphs 57, to 61, of EP 1304542, A2, claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80, A/m and a gradient (in a given space direction) of the field strength of the magnetic selection field 211 amounting to 160 $10^3$, A/m2,, the first sub-zone 301 in which the magnetization of the particles 100 is not saturated has dimensions of about 1, mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220''' which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220''' are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220", 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220''' are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100, Hz. The magnetic field generated by the drive means 220 varies preferably between approximately 25, kHz and approximately 100, kHz. The magnetic field variations that the receiving means are supposed to be sensitive are preferably in a frequency range of approximately 50, kHz to approximately 10, MHz.

FIGS. 4a, and 4b, show the magnetization characteristic, that is, the variation of the magnetization M of a particle 100 (not shown in FIGS. 4a, and 4b) as a function of the field strength H at the location of that particle 100, in a dispersion with such particles. It appears that the magnetization M no longer changes beyond a field strength $+H_c$, and below a field strength $-H_c$, which means that a saturated magnetization is reached. The magnetization M is not saturated between the values $+H_c$, and $-H_c$.

FIG. 4a, illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$, and slightly to the left when the magnetic field H decreases from $+H_c$, to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b, shows the effect of a sinusoidal magnetic field H(t) on which a static magnetic field $H_1$, is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

One important object according to the present invention is to provide an inventive arrangement such that the respective resistances of the selection means 210 (if the magnetic selection field is generated by means of a current), the drive means 220 and the receiving means 230 are as low as possible. It is proposed according to the present invention to provide at least one of the selection means 210, the drive means 220 and/or the receiving means 230 at least partially with litz wire 250 which is explained in greater details in FIGS. 5 to 7.

In FIGS. 5 to 7 the litz wire 250 of one or a plurality of the selection means 210, the drive means 220 and/or the receiving means 230 according to the present invention is shown in a schematical representation. Each of these figures represents a cross sectional view of one embodiment of such a litz wire 250 according to the present invention. Each litz wire 250 comprises a multitude of individual wires 255. The representations of the various embodiments are not drawn to scale and the dimensions are chosen for the sake of representation simplicity only. The filling factor of the litz wire 250 can easily be evaluated by means of summing up the cross sectional areas of each of the individual wires 255 and dividing by the cross sectional area of the complete litz wire 250. By means of applying a pressure to the embodiments of the litz wire 250 represented in FIGS. 5 to 7 in a direction perpendicularly to the longitudinal extension of the litz wire 250, the filling factor can be enhanced. Each individual wire 255 is preferably surrounded circumferentially by an electrically high resistive material 256 which acts in the manner of a cladding 256 for each individual wire 255. It is to be understood that it is preferred according to the present invention that such a cladding material 256 is present at each individual wire 255; however such a continuous cladding 256 is not necessary if the condition is fulfilled that each individual wire 255 of the litz wire 250 is electrically isolated from the adjacent individual wires 250 between a first end 250' of the litz wire and a second end 250" of the litz wire 250. The individual wires 255 of the litz wire 250 act as individual current supporting paths 255 and can be regarded as resistors connected in parallel and having ideally an identical impedance as shown by the equivalent circuit diagram represented on the right hand side in FIG. 5. Therefore it is preferred according to the present invention, that the litz wire is spun such that one individual wire is e.g. in the center of the litz wire at one position along the extension direction of the litz wire and that this individual wire is e.g. in the periphery of the litz wire at another position along the extension direction of the litz wire. In the embodiment of the litz wire 250 represented in FIG. 5, a further preferred feature of the litz wire 250 is represented, namely a plastic foil insulation 257 is provided collectively around the individual wires 255. Such a plastic (e.g. thermoplastic) insulation can also be provided to all the other embodiments of the litz wire 250 but is not shown there. The additional feature of such an insulation foil or insulation material 257 collectively around the individual wires 255 of the litz wire 250 provides the advantage that a better high voltage performance of the litz wire is possible.

In FIG. 6 a cross sectional view of a further embodiment of the litz wire 250 is schematically shown where the litz wire 250 comprises also a plurality of individual wires 255 (as in the embodiment according to FIG. 5) but with the individual wires 255 grouped in a plurality of so-called first order litz wires 251. These first order litz wires 251 (each comprising a plurality of individual wires 255) are combined together to form the litz wire 250. In FIG. 6, the continuous cladding 256 is preferably present around each individual wire 255 but not indicated by means of a reference numeral.

In FIG. 7 a cross sectional view of a still further embodiment of the litz wire 250 is schematically shown where the litz wire 250 comprises also a plurality of individual wires 255 (as in the embodiments according to FIGS. 5 and 6) and a plurality of first order litz wires 251 but with the first order litz wires 251 grouped in a plurality of so-called second order litz wires 252. These second order litz wires 252 (each comprising a plurality of first order litz wires 251) are combined together to form the litz wire 250. In FIG. 6, the continuous cladding 256 is preferably present around each individual wire 255 but not represented for the sake of simplicity.

Figure 8:
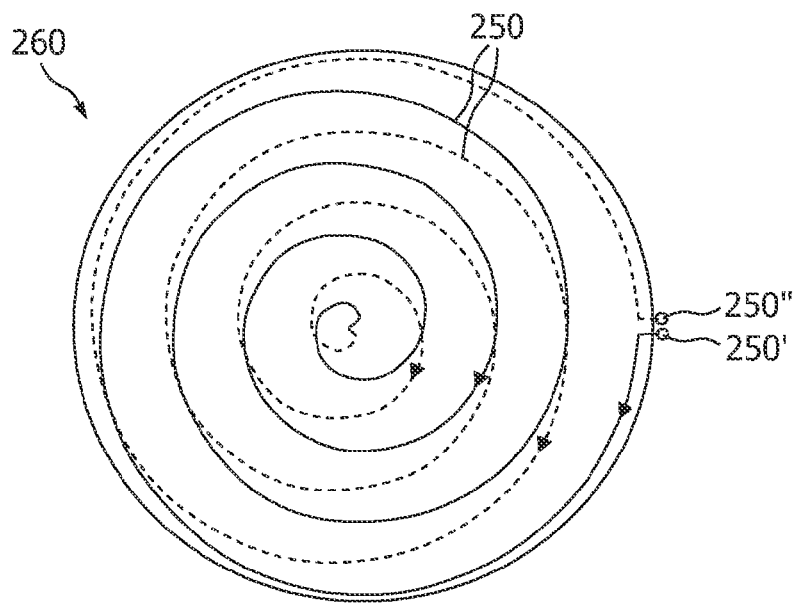
Figure 9:
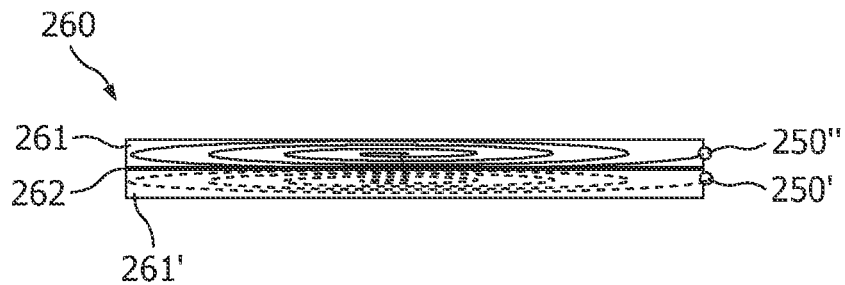

In FIGS. 8 to 11 different embodiments of disk shaped coils 260 comprising a litz wire 250 are shown. FIG. 8 schematically shows a top view of a disk shaped coil 260 comprising a litz wire 250, the litz wire 250 comprising again the first end 250' and the second end 250''. FIG. 9 schematically shows a side view of the disk shaped coil 260 depicted in FIG. 8. As one example of a possible pattern of the litz wire 250, FIGS. 8 and 9 show a litz wire 250 patterned such that it is wound spirally with both the first and the second end 250', 250'' lying on the outside of the disk (i.e. essentially at a maximum radius of the disk). In one embodiment, this can be realised by means of arranging the litz wire 250 in two layers 261, 261' (shown only in FIG. 9). In a first of the two layers 261, 261' the litz wire 250 is wound e.g. spirally radialy from the exterior of the disk shaped coil 260 towards smaller radiuses of the disk shaped coil 260 (drawn through line of the litz wire 250) wherein in the second of the two layers 261, 261', the litz wire 250 is wound spirally in the opposite direction, i.e. from smaller radiuses towards greater radiuses (dashed line of the litz wire 250). In the embodiment shown, an insulating foil 262 is provided between the two layers 261, 261' of the disk shaped coil 260. This enhances the high voltage performance and can reduce parasitic capacitances. However, the provision of the insulating foil 262 is not mandatory.

Figure 10:
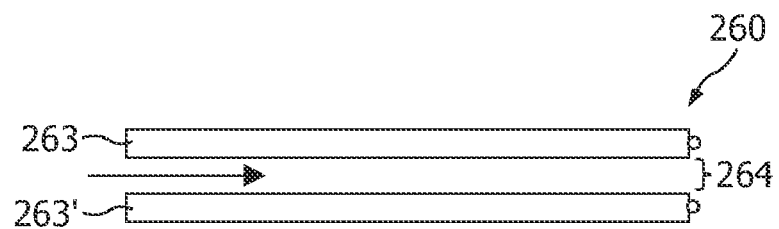
Figure 11:
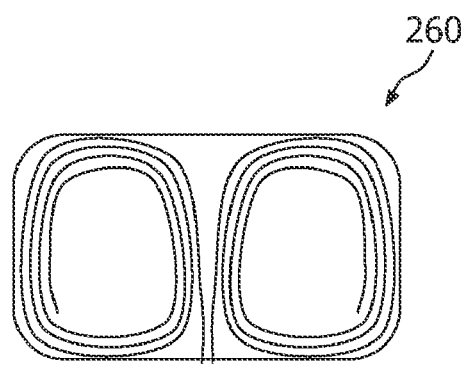

FIGS. 10 and 11 schematically show further examples of disk shaped coils 260. In FIG. 10, two spaced disks 263, 263' are provided with a cooling channel 264 between them. The flow of a cooling fluid (gas or liquid, especially water and/or oil) is schematically indicated by a horizontal arrow. It is also possible to provide spacers (not shown) in order to position de two spaced disks 263, 263' at a defined position relative to one another and relative to other components of the inventive arrangement 10. The cooling channels 264 can be provided by means of removing portions of the disk shaped coil 260. For example, this can be realised by means of combining a soluble or etchable material together with the material of the disk shaped coil 260 and by means of opening the cooling channels by resolving of by etching the soluble or etchable material. In FIG. 11, a double D pattern of the litz wire 250 is schematically shown. Such a pattern provides the possibility of enhancing the accessibility of the region of action 300 as the region of action does not need to be completely surrounded by coils and still a three-dimensional resolution of the arrangement 10 is possible with the drive means 220 providing magnetic drive field 221 components in three space directions perpendicular to each other.

In FIG. 12, a schematical representation of an example of a method of producing the disk shaped coil 260 is shown. The pattern 266 of the litz wire 250 is placed in a first half 267 of a mould, where the first half 267 is essentially extending along a plane 265 defining later the main plane of the disk shaped coil 260. The litz wire 250 pattern 266 comprises preferably a first thermoplastic material 258 which can preferably be comprised by the litz wire 250 (e.g. by means of thermoplastic resin wires interwoven with the metallic current supporting individual wires 255) or which can be added to the litz wire 250 pattern 266 before applying a pressure in order to definitely form the shape of the disk shaped coil 260. The pressure is represented by the two vertical arrows in FIG. 12 and is applied between the first half 267 and a second half 268 of the mould or tool. By applying the pressure the disk shaped coil 260 is definitely formed and curable materials cured. In an alternative embodiment, the application of a second thermoplastic material 259 (in addition to the first thermoplastic material 258 or instead of the first thermoplastic material 258) during the application of the pressure is realised.

The invention claimed is:

1. An arrangement (10) for influencing and/or detecting magnetic particles (100) in a region of action (300), which arrangement comprises:
   selection means (210) for generating a magnetic selection field (211) having a pattern in space of its magnetic field strength such that a first sub-zone (301) having a low magnetic field strength and a second sub-zone (302) having a higher magnetic field strength are formed in the region of action (300),
   drive means (220) for changing the position in space of the two sub-zones (301, 302) in the region of action (300) by means of a magnetic drive field (221) so that the magnetization of the magnetic particles (100) changes locally,
   receiving means (230) for detecting signals from the magnetic particles (100), which signals depend on the magnetization in the region of action (300), which magnetization is influenced by the change in the position in space of the first and second sub-zone (301, 302),
   wherein the selection means (210) and/or the drive means (220) and/or the receiving means (230) comprises at least partially a litz wire/stranded wire (250), and
   wherein the signals detected from the magnetic particles (100) located in the sub-zone (301) are detected in another frequency band than a frequency band of the magnetic drive field (221).

2. An arrangement (10) according to claim 1, wherein the litz wire (250) comprises a plurality of individual wires (255), each individual wire being surrounded by an electrically high resistive material (256).

3. An arrangement (10) according to claim 2, wherein the litz wire (250) comprises a plurality of first order litz wires (251) comprising a plurality of individual wires (255), wherein the litz wire (250) comprises a plurality of first order litz wires (251).

4. An arrangement(10) according to claim 2, wherein the litz wire (250) comprises a plurality of first order litz wires (251) and a plurality of second order litz wires (252), wherein the first order litz wires (251) comprise a plurality of individual wires (255), wherein the second order litz wires (252) comprise a plurality of first order litz wires (251), and wherein the litz wire (250) comprises a plurality of second order litz wires (252).

5. An arrangement (10) according to claim 1, wherein the resistance of the receiving means (230) is dominated by thermal noise, especially generated by thermal noise in the region of action (300).

6. An arrangement (10) according to claim 1, wherein the litz wire (250) comprises at least partially a ferromagnetic material.

7. An arrangement (10) according to claim 1, wherein the litz wire (250) is at Least partially used for the selection means (210) and/or for the drive means (220) and wherein the litz wire (250) of the selections means (210) is at least partially penetrated by the magnetic drive field (221) of the drive means (220) and/or wherein the litz wire (250) of the drive means (220) is at least partially penetrated by the magnetic selection field (211) of the selection means (210).

8. An arrangement (10) according to claim 1, wherein the litz wire (250) is arranged such that the resistance in a given working frequency band and in a given electromagnetic field penetrating the litz wire (250) is substantially minimal.

9. An arrangement (10) according to claim 1, wherein the litz wire (250) has a ratio of the summed cross sectional area of the individual wires (255) relative to the cross sectional area of the litz wire (250) (filling factor) of about 0.30 to about 0.70 or wherein the litz wire (250) has a ratio of the summed cross sectional area of the individual wires (255) relative to the cross sectional area of the litz wire (250) (filling factor) of about 0.01 to about 0.20.

10. An arrangement (10) according to claim 1, wherein the individual wires (255) of the litz wire (250) has a diameter of approximately 1 μm to approximately 50 μm.

11. An arrangement (10) according to claim 1, wherein the litz wire (250) is a compressed litz wire (250).

12. An arrangement (10) according to claim 1, wherein the litz wire (250) comprises a multitude of thermoplastic resin wires.

13. An arrangement (10) according to claim 1, wherein space between different litz wires (250) or space inside the litz wire (250) is used for one or a plurality of cooling channels.

14. An arrangement (10) according to claim 1, wherein the selection means (210) and/or the drive means (220) and/or the receiving means (230) comprises an at least partially disk shaped coil (260).

15. A method for influencing and/or detecting magnetic particles (100) in a region of action (300), wherein the method comprises the steps of generating a magnetic selection field (211) having a pattern in space of its magnetic field strength such that a first sub-zone (301) having a low magnetic field strength and a second sub-zone (302) having a higher magnetic field strength are formed in the region of action (300), changing the position in space of the two sub-zones (301, 302) in the region of action (300) by means of a magnetic drive field (221) so that the magnetization of the magnetic particles (100) changes locally, detecting signals from the magnetic particles (100), which signals depend on the magnetization in the region of action (300), which magnetization is influenced by the change in the position in space of the first and second sub-zone (301, 302), wherein the generation of the magnetic selection field (211) and/or the change of the position in space of the two sub-zones (301, 302) and/or the acquisition of the signals depending on the magnetization in the region of action (300) is performed at least partially by means of a litz wire/stranded wire (250), and wherein the signals detected from the magnetic particles (100) located in the first sub-zone (301) are detected in another frequency band than a frequency band of the magnetic drive field (221).

\* \* \* \* \*